US006573706B2

(12) United States Patent
Mendes et al.

(10) Patent No.: US 6,573,706 B2
(45) Date of Patent: Jun. 3, 2003

(54) METHOD AND APPARATUS FOR DISTANCE BASED DETECTION OF WEAR AND THE LIKE IN JOINTS

(75) Inventors: Emanuel Mendes, Petah Tikvah (IL); David Mendes, Haifa (IL); Ruth Beer, Haifa (IL); Gilad Barak, Hanagid (IL)

(73) Assignee: IntelliJoint Systems Ltd., Haifa (IL)

( * ) Notice: Subject to any disclaimer, the term of this patent is extended or adjusted under 35 U.S.C. 154(b) by 0 days.

(21) Appl. No.: 09/774,017

(22) Filed: Jan. 31, 2001

(65) Prior Publication Data

US 2002/0101232 A1 Aug. 1, 2002

Related U.S. Application Data

(63) Continuation-in-part of application No. PCT/IL00/00757, filed on Nov. 15, 2000, which is a continuation-in-part of application No. 09/585,318, filed on Jun. 2, 2000, now Pat. No. 6,245,109, which is a continuation of application No. 09/443,113, filed on Nov. 18, 1999, now abandoned.

(51) Int. Cl.[7] .............................. G01B 7/00; G01B 7/14; A61B 5/103
(52) U.S. Cl. .............................. 324/207.17; 324/207.22; 324/207.26; 600/595
(58) Field of Search .......... 324/207.16, 207.17–207.19, 324/207.22–207.26, 219, 234, 236, 239, 655; 340/551, 572.5; 600/409, 424, 595; 901/35, 46

(56) References Cited

U.S. PATENT DOCUMENTS

| | | | | |
|---|---|---|---|---|
| 3,740,742 A | * | 6/1973 | Thompson et al. | 324/67 X |
| 4,618,822 A | * | 10/1986 | Hansen | 324/207.16 |
| 4,843,259 A | * | 6/1989 | Weisshaupt | 324/207.26 X |
| 4,950,986 A | * | 8/1990 | Guerrero | 324/207.19 |
| 5,019,782 A | * | 5/1991 | Schatter | 324/655 |
| 5,180,978 A | * | 1/1993 | Postma et al. | 324/207.16 |
| 5,726,567 A | * | 3/1998 | Lewis et al. | 324/207.16 |
| 5,935,171 A | * | 8/1999 | Schneider et al. | |
| 6,245,109 B1 | * | 6/2001 | Mendes et al. | |

FOREIGN PATENT DOCUMENTS

DE 3213602 * 10/1983

* cited by examiner

*Primary Examiner*—Gerard R. Strecker
(74) *Attorney, Agent, or Firm*—G. E. Ehrlich Ltd.

(57) ABSTRACT

A distance measurement system, comprising at least one resonant circuit, at least one magnetic element with predetermined magnetic properties, a transmitter operable to transmit an electromagnetic pulse, a receiver operable to detect oscillations emitted by said resonant circuit in response to said electromagnetic pulse, and an analyzer operable to analyze an amplitude envelope property of said oscillations, to thereby determine a distance between the resonant circuit and the magnetic element.

26 Claims, 4 Drawing Sheets

METHOD AND APPARATUS FOR DISTANCE BASED DETECTION OF WEAR AND THE LIKE IN JOINTS

RELATIONSHIP TO EXISTING APPLICATIONS

The present application is a continuation in part of PCT/IL00/00757 filed Nov. 15, 2000, and is a continuation in part of U.S. patent application Ser. No. 09/585,318 filed Jun. 2, 2000, now U.S. Pat. No. 6,245,109, which is a continuation of U.S. patent application Ser. No. 09/443,113 filed Nov. 18, 1999, now abandoned.

FIELD OF THE INVENTION

The present invention relates to a distance measurement system and more particularly but not exclusively to determining a distance between the core of a resonant circuit and a ferromagnetic or paramagnetic element.

BACKGROUND OF THE INVENTION

Mechanical fixtures such as joints and bearings often suffer from performance degradation due to material wear. When the wear becomes pronounced this may result in loss of efficiency or damage to the system in which it is installed. This wear may be difficult to measure, as it generally involves small displacement changes and develops slowly over time. Additionally, the fixtures may be in inaccessible locations. Thus, in order to detect such wear, a sensor is needed which can detect small changes in the distance between two interior locations.

Koeplin, et al. in U.S. Pat. No. 4,914,951 describes an ultrasonic sensor for measuring the distance from a transducer to an object. These sensors have particular applicability for motor vehicles. The invention uses at least one electroacoustic transducer to transmit an ultrasonic signal and to receive the ultrasonic signal reflected by an object. An electric generator is used to activate the transducer. A receiving stage is provided for the echo signals picked up by the transducer. A control unit uses the generator to activate the transducer for a predetermined transmission time. The transducer then decays for a time following its activation to provide a reception window for receiving the reflected echo signals. Ultrasonic signals are not always suitable for detecting material wear.

SUMMARY OF THE INVENTION

According to a first aspect of the present invention there is thus provided a distance measurement system, comprising at least one resonant circuit, at least one magnetic element with predetermined magnetic properties, a transmitter operable to transmit an electromagnetic pulse, a receiver operable to detect oscillations emitted by the resonant circuit in response to the electromagnetic pulse, and an analyzer operable to analyze an amplitude envelope property of the oscillations, to thereby determine a distance between the resonant circuit and the magnetic element. In an embodiment, the magnetic element is ferromagnetic. In another embodiment the magnetic element is paramagnetic. In an additional embodiment, the analyzer is operable to determine the amplitude envelope property from an absolute value of amplitudes of the oscillations. In another embodiment the analyzer is operable to determine the amplitude envelope property from relative amplitude values of more than one cycle of the oscillations. In an embodiment the amplitude envelope property is an amplitude rate of decay. In an additional embodiment the analyzer is operable to determine the distance between the resonant circuit and the magnetic element additionally from frequency properties of the oscillations.

In a preferred embodiment the distance measurement system comprises more than one resonant circuit, to thereby determine more than one distance between the resonant circuits and the at least one magnetic element. Another embodiment is operable to determine the distance between the resonant circuits and the at least one magnetic element in more than one dimension. In another embodiment the more than one resonant circuits are operable to resonate at different frequencies.

Another embodiment comprises more than one magnetic element, to thereby determine more than one distance between the at least one resonant circuit and the magnetic elements. Another embodiment preferably is operable to determine the distance between the at least one resonant circuit and the magnetic elements in more than one dimension.

Another embodiment comprises more than one resonant circuit and more than one magnetic element, to thereby determine more than one distance between the resonant circuits and the magnetic elements. Another embodiment preferably is operable to determine the distance between the resonant circuits and the at least one magnetic element in more than one dimension.

In a preferred embodiment the analyzer comprises a look-up table, comprising relationships between measured oscillations and distances. In another embodiment the relationships are per-system relationships. In an additional embodiment, the relationships comprise in-situ calibrations.

According to a second aspect of the present invention there is thus provided a method for assembling a distance measurement system, comprising the steps of: placing a resonant circuit at a first location, placing a magnetic element with predetermined magnetic properties at a second location, providing a transmitter for transmitting an electromagnetic pulse to the resonant circuit, providing a detector for detecting oscillations emitted by the resonant circuit in response to the electromagnetic pulse, and providing an analyzer for analyzing an amplitude envelope property of the detected oscillations, to thereby determine a distance between the first location and the second location. In an embodiment, the analyzer comprises a look-up table of relationships between measured oscillations and distances, and wherein the look-up table values are established for each one of a predetermined set of distances by performing for each predetermined distance the steps of: transmitting an electromagnetic pulse to the resonant circuit, detecting oscillations emitted by the resonant circuit in response to the electromagnetic pulse, and measuring an amplitude envelope property of the detected oscillations, to thereby establish a look-up table value for the distance.

According to a third aspect of the present invention there is thus provided a method for measuring the distance between a first location comprising a resonant circuit and a second location comprising a magnetic element, comprising the steps of: transmitting an electromagnetic pulse to the resonant circuit, detecting oscillations emitted by the resonant circuit in response to the electromagnetic pulse, and analyzing an amplitude envelope property of the detected oscillations, to thereby determine a distance between the first location and the second location. In a preferred embodiment, the step of analyzing an amplitude envelope property further comprises comparing information detected from the emitted oscillations to information in a look-up table, of relationships between measured oscillations and distances. Another embodiment comprises obtaining the amplitude envelope property from an absolute value of amplitudes of the oscillations. Another preferred embodiment comprises obtaining the amplitude envelope property from relative amplitude values of more than one cycle of the oscillations. Another embodiment, comprises making use of an amplitude rate of decay as the amplitude envelope property. Another embodiment comprises additionally detecting the distance from frequency properties of the detected oscillations.

According to a fourth aspect of the present invention there is thus provided a distance measurement system utilizing eddy currents for energy dissipation, the system comprising: at least one resonant circuit, at least one magnetic element with predetermined magnetic properties, a transmitter operable to transmit an electromagnetic pulse, a receiver operable to detect oscillations emitted by the resonant circuit in response to the electromagnetic pulse, and an analyzer operable to analyze an amplitude envelope property of the oscillations as an indicator of eddy current induced energy dissipation, to thereby determine a distance between the resonant circuit and the magnetic element.

BRIEF DESCRIPTION OF THE DRAWINGS

For a better understanding of the invention and to show how the same may be carried into effect, reference will now be made, purely by way of example, to the accompanying drawings, in which.

DESCRIPTION OF THE PREFERRED EMBODIMENTS

When a resonant circuit is energized by a short pulse, the circuit begins to oscillate at the free resonant frequency. The free oscillation frequency of a resonant circuit is:

$$f = 0.5 * \Pi * (L * C)^{0.5}$$

If no additional external energy is provided, the amplitude of the oscillation will decay. The amplitude rate of decay, absolute amplitude, and exact resonance frequency are influenced by two main factors. The first factor is the internal equivalent resistance of the circuit due to circuit elements. The second factor is the external equivalent resistance due to eddy currents at elements that interfere with the magnetic field of the resonant circuit. Magnetic elements in proximity to the resonant circuit create such interference, and influence the resonant circuit response to the energizing pulse. The characteristics of the oscillation induced in the resonant circuit by the energizing pulse may be used to measure the distance between a resonant circuit and a magnetic element. This physical principle is the basis for the distance measurement system described below.

Figure 1:
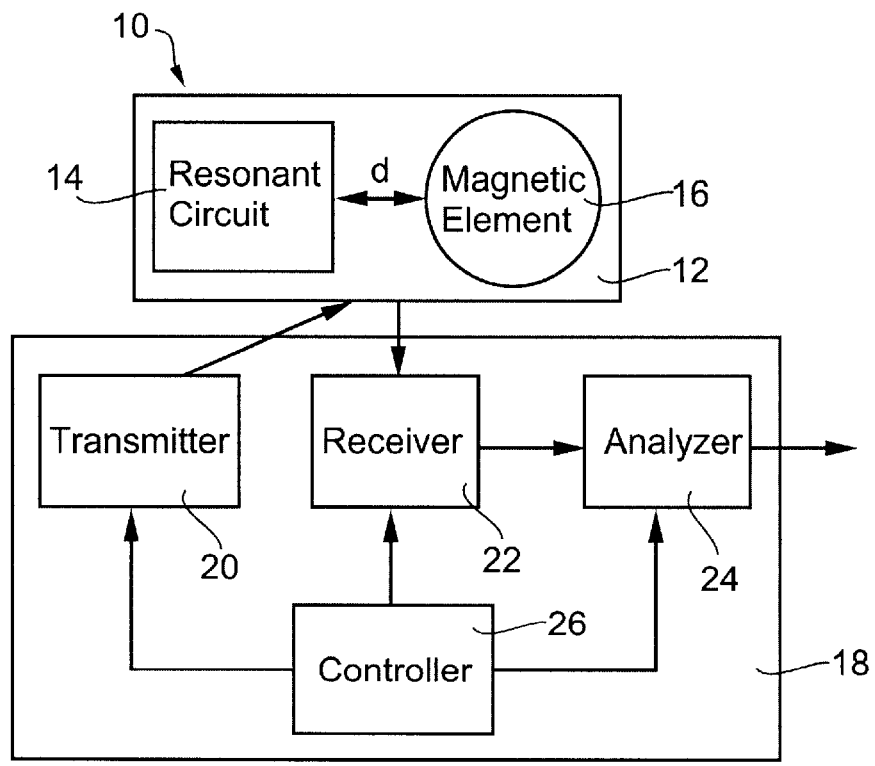
FIG. 1 is a simplified block diagram of a preferred embodiment of a distance measurement system.

Reference is now made to FIG. 1, which is a simplified block diagram of a preferred embodiment of a distance measurement system. A distance measurement system 10 comprises two subsystems, a sensor subsystem 12 and an analysis subsystem 18. The sensor subsystem 12 comprises at least one resonant circuit 14 and at least one magnetic element 16, separated by a distance d that is to be detected by the measurement system. The analysis subsystem 18 comprises a transmitter 20, receiver 22, and analyzer 24, all of which are controlled by controller 26.

Transmitter 20 transmits a short electromagnetic pulse that energizes the resonant circuit 14. In response to the pulse, sensor subsystem 12 emits a damped oscillation, which is received by receiver 22. The characteristics of the emitted signal depend upon the properties of resonant circuit 14 and magnetic element 16, and upon the distance d between them. The received signal is analyzed by analyzer 24, which analyzes its characteristics to determine the distance d, as will be described in detail below. Controller 26 controls and coordinates all analysis subsystem 18 functions.

Figure 2:
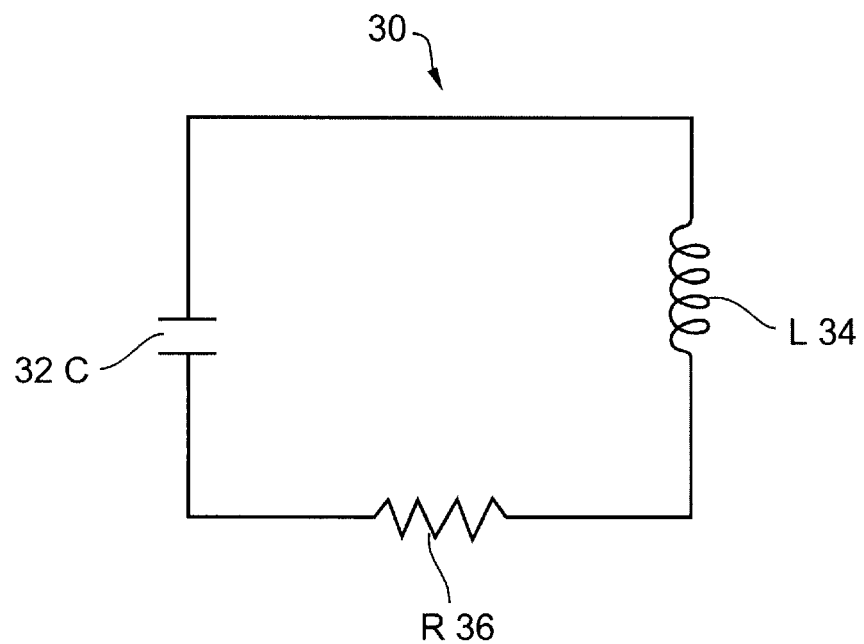
FIG. 2 is a simplified diagram of a resonant circuit.

Reference is now made to FIG. 2, which is a simplified diagram of a preferred embodiment of a resonant circuit 30. The resonant circuit shown is a simple RLC circuit comprising a capacitor C 32, an inductor L 34, and a resistor R 36. The resonant frequency of resonant circuit 30 depends primarily on the values of capacitor C 32 and inductor L 34, as defined in the above equation. The value of resistor R 36, along with other dissipative effects such as eddy currents in elements which interfere with the circuit's magnetic field, determines the circuit's amplitude rate of decay, as discussed above.

Figure 3:
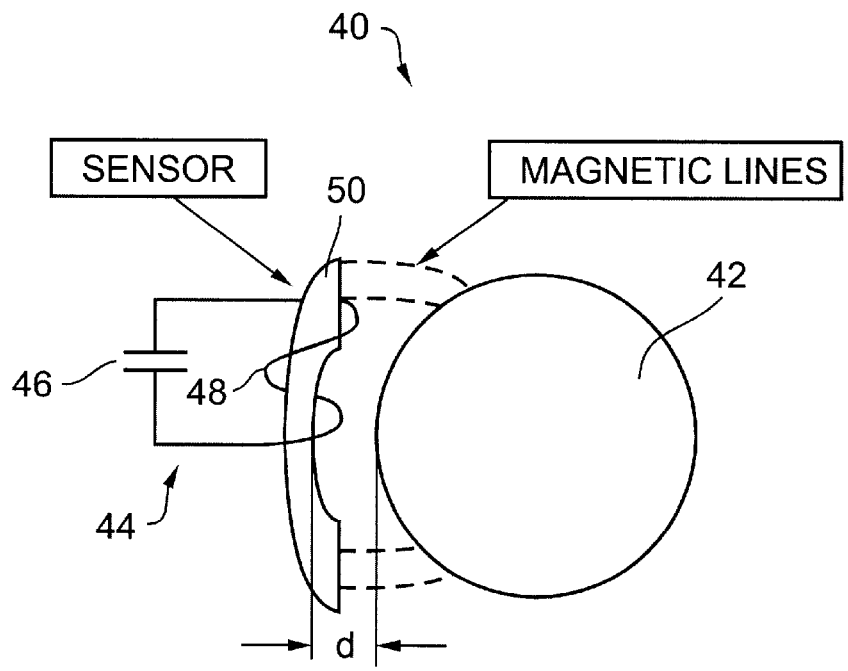
FIG. 3 is a simplified diagram of a sensor subsystem.

Reference is now made to FIG. 3, which is a simplified diagram of a preferred embodiment of a sensor subsystem 40. Magnetic element 42 comprises a material with known magnetic properties. In one preferred embodiment the material is ferromagnetic. In another preferred embodiment the material is paramagnetic. Resonant circuit 44 comprises a capacitor 46 and a coil 48 wound on a core 50. When the resonant circuit 44 is energized by a pulse of electromagnetic radiation, the circuit emits a damped oscillatory electromagnetic signal. The characteristics of the emitted signal may be affected by the distance between magnetic element 42 and resonant circuit 44.

Figure 4:
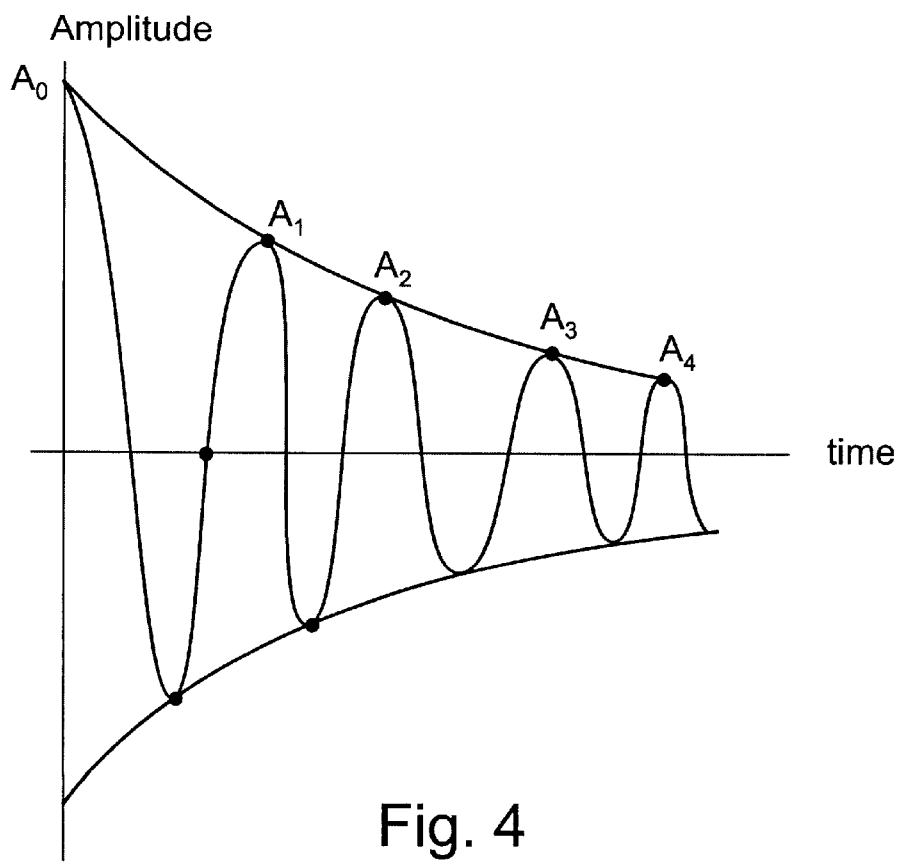
FIG. 4 shows an example of a damped oscillation.

Reference is now made to FIG. 4, which shows an example of a damped oscillation. The oscillation shown has two main characteristics. The first characteristic is the rate at which the amplitude of the oscillation decreases over time. The second characteristic is the frequency of the oscillation.

As shown in FIG. 4, the amplitude of the generated damped oscillations may be represented by a decreasing series of values, $A_0$ to $A_n$. The amplitude of the initial oscillation is $A_0$ and the amplitude of the $n^{th}$ oscillation is $A_n$, where n equals four in FIG. 4. The amplitude of the damped oscillations is a function of the energy absorbed at each cycle by the internal equivalent resistance of the resonant circuit 44, and by the external equivalent resistance due to eddy currents at elements that interfere with the magnetic field of resonant circuit 44, primarily the magnetic element 42. The amount of interference by magnetic element 42 is a function of the distance d between the magnetic element 42 and the resonant circuit 44. Distance d may thus be determined from measurements of the amplitudes $A_i$, of the oscillations produced by sensor subsystem 40. Any reference to amplitude values in this or later embodiments may be to peak-to-peak amplitude, negative peak amplitude, positive peak amplitude, or any other amplitude indicator.

Figure 5:
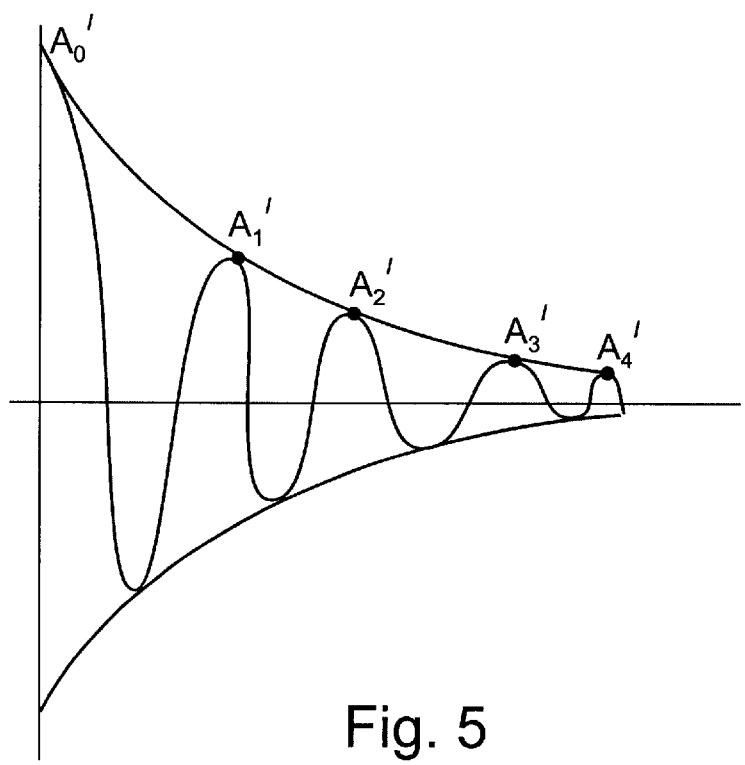
FIG. 5 shows a second example of a damped oscillation.

In one preferred embodiment distance d is determined from the absolute value of the amplitudes of one or more cycles of oscillation produced by sensor subsystem 40. Reference is now made to FIG. 5, which shows a second example of a damped oscillation. The absolute amplitudes of the oscillations $A_i'$ differ from the absolute amplitudes $A_i$ in FIG. 4. Changing the distance d between the resonant circuit 30 and the magnetic element 42 affects the absolute signal amplitudes. Distance d may be detected by analyzing the absolute amplitudes of the emissions received from the sensor subsystem 40.

In a second preferred embodiment, the distance d is measured by analyzing the relative values of the amplitudes of successive cycles of emissions received from the sensor subsystem 40. In the preferred embodiment, the relative amplitudes are compared by examining the ratios:

$$A_r(ik) = A_i/A_{i+k}$$

where $A_i$ is the amplitude of the i-th oscillation, and $A_{i+k}$ is the amplitude after k subsequent oscillations. Higher resolution may be obtained by increasing k, however k is preferably not increased to the point where noise effects compromise amplitude measurements.

In another preferred embodiment, frequency information is additionally used to determine the distance between the sensor subsystem elements. The distance d may change the oscillation frequency due to the proximity of the magnetic element 42 to the resonant circuit 44. The oscillation frequency of resonant circuit 44 is determined primarily by the values of the capacitor 46 and the coil 48. However the distance of the magnetic element 42 from the resonant circuit 44 also influences the values of the reactive elements of the circuit. The values of the reactive elements, and hence the emitted frequency, depend upon both the magnetic characteristics of the magnetic element 42, and its distance from the resonant circuit 44. If the magnetic properties of magnetic element 42 are known, the emitted frequency may be used as an additional indicator of the distance d.

Figure 6:
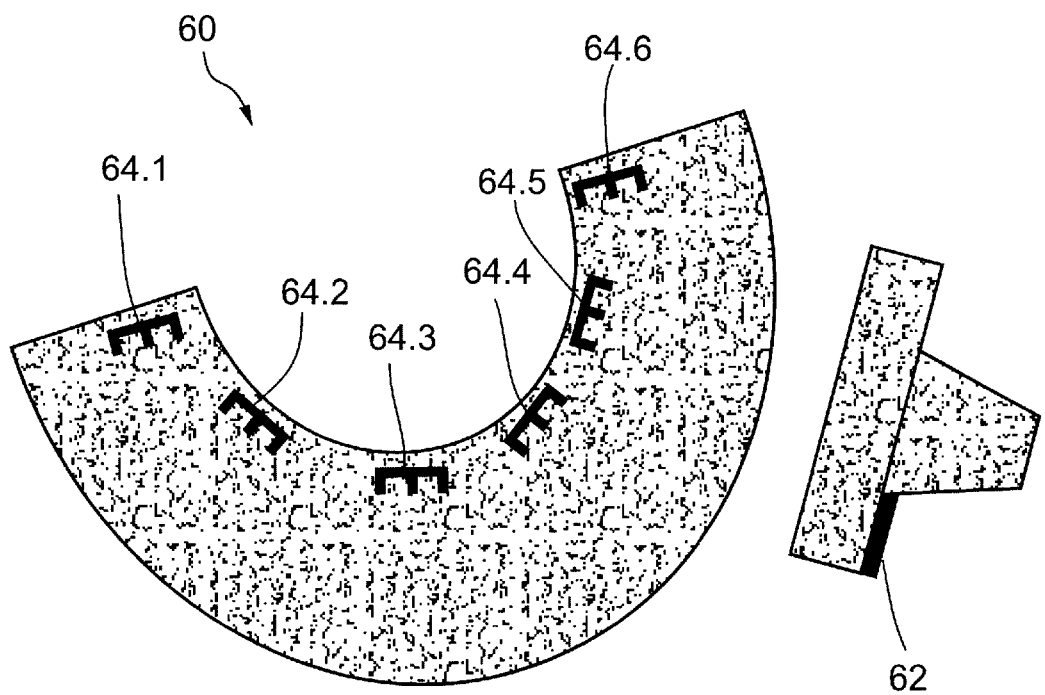
FIG. 6 is a simplified sensor subsystem with more than one resonant circuit.

Reference is now made to FIG. 6, which is a simplified preferred embodiment of a sensor subsystem 60 with more than one resonant circuit. The subsystem comprises one magnetic element 62 and several resonant circuits 64.1 . . . 64.6. In a preferred embodiment each resonant circuit is tuned to a different frequency. The number of resonant circuits may vary over different configurations. Each resonant circuit 64.i is located at a distance $d_i$ from the magnetic element 62. Each resonant circuit emits a damped oscillation in response to a transmitted electromagnetic pulse. The total emission from the sensor subsystem 60 depends upon the distances $d_i$. In the current embodiment the distances $d_i$ may be measured simultaneously by analyzing the sensor subsystem emissions. In the preferred embodiment the resonant circuits 64 are designed to emit at different free oscillation frequencies in order to distinguish the signal emitted by each resonant circuit 64. If the free oscillation frequencies are adequately separated and the resonant circuits tuned accordingly, the emission parameters of each resonant circuit may be easily distinguished.

The preferred embodiment can be used for determining a distance, or for monitoring a change in a distance, between any objects which are placed several millimeters to several meters apart, while providing highly accurate distance measurements with a resolution of several microns or less. The effectiveness of the preferred embodiment at various distance ranges depends mainly on the size and configuration of the sensor subsystem elements employed.

In another preferred embodiment the sensor subsystem comprises more than one magnetic element. Each magnetic element i is located at a distance $d_i$ from the resonant circuit. The resonant circuit emits a damped oscillation in response to the transmitted electromagnetic pulse. The characteristics of the sensor subsystem emission depend upon the distances $d_i$. The distances $d_i$ may be measured simultaneously by analyzing the total emission output from the sensor subsystem.

In another embodiment the sensor subsystem comprises more than one magnetic element and more than one resonant circuit. Each magnetic element i is located at a distance $d_{ik}$ from resonant circuit k. The resonant circuits emit damped oscillations in response to the transmitted electromagnetic pulse. The characteristics of the total emission from the sensor subsystem depend upon the distances $d_{ik}$. The distances $d_{ik}$ may be measured simultaneously by analyzing the total emission output from the sensor subsystem.

In a preferred embodiment, a dedicated look-up table is used to facilitate the analysis of the emitted signal, and to eliminate variations due to production tolerances. The look-up table stores information about emitted signal characteristics at several distances. Intermediate distances may be calculated by interpolation. The look-up table may be used to compensate for non-linearities in the resonant circuit response as a function of distance from the magnetic element. In the preferred embodiment the signal characteristic stored in the look-up table is the value of a preselected amplitude ratio, for example $A_0/A_{20}$. In one preferred embodiment the values stored in the look-up are expected signal characteristics. In another preferred embodiment, the values stored in the look-up table are specific to each device. These values are determined by testing each device after manufacture. In another embodiment, the distance d is determined by linear interpolation of the amplitude.

Figure 7:
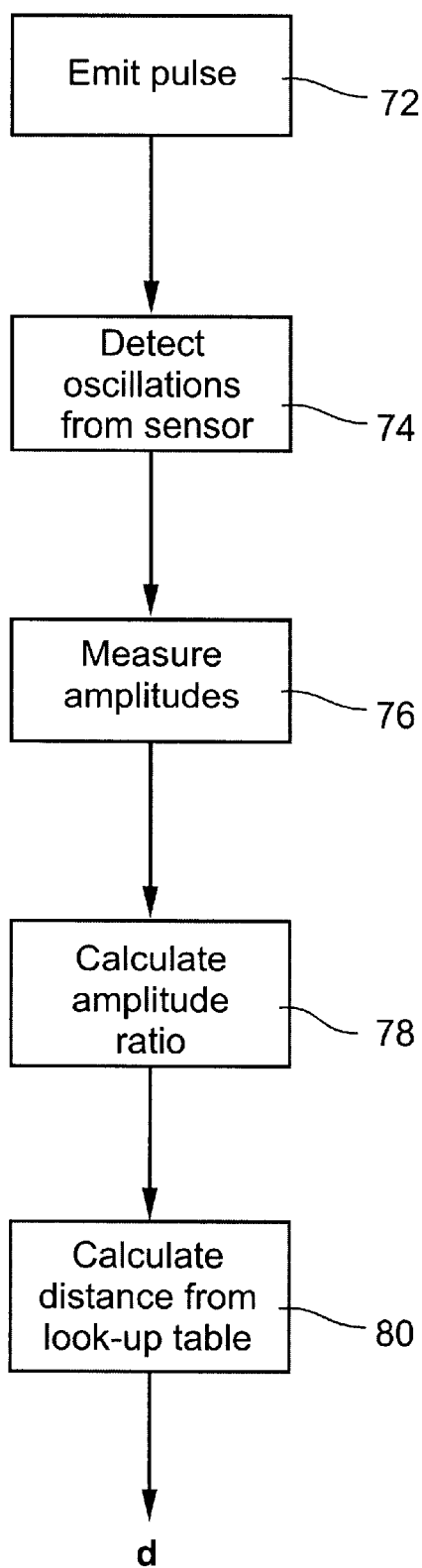
FIG. 7 is a simplified flow chart of the distance measurement process.

Reference is now made to FIG. 7, which is a simplified flow chart of an embodiment of the distance measurement process using the system described above. First an electromagnetic pulse is emitted in the vicinity of the sensor subsystem in step 72. The sensor subsystem emits a damped oscillation in response to the pulse, which is detected in step 74. The amplitudes of the required cycles of the detected oscillation are measured in step 76. Dividing the measured amplitudes forms an amplitude ratio in step 78. The look-up table is used to convert this ratio into a distance measurement in step 80.

The embodiments of distance measurement systems described above all utilize the effect of eddy currents on resonant circuit emissions to measure the distance between one or more resonant circuits and one or more magnetic elements. Various signal parameters, such as absolute amplitude, relative amplitude, and frequency may be utilized to determine the distance between each resonant circuit and each magnetic element.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

We claim:

1. A distance measurement system, comprising:
   at least one resonant circuit;
   at least one magnetic element with predetermined magnetic properties located remotely from said resonant circuit by a first distance; and
   a separate device, not connected to said resonant circuit, said separate device comprising:
      a transmitter operable to transmit an electromagnetic pulse;
      a receiver operable to detect oscillations emitted by said resonant circuit in response to said electromagnetic pulse; and,
      an analyzer operable to analyze an amplitude envelope decay pattern of said oscillations following said electromagnetic pulse, therefrom to determine an eddy current factor effecting said decay pattern and therefrom to determine said first distance.

2. A distance measurement system according to claim 1, wherein said magnetic element is ferromagnetic.

3. A distance measurement system according to claim 1, wherein said magnetic element is paramagnetic.

4. A distance measurement system according to claim 1, wherein said analyzer is operable to determine said amplitude envelope property from an absolute value of amplitudes of said oscillations.

5. A distance measurement system according to claim 1, wherein said analyzer is operable to determine said amplitude envelope property from relative amplitude values of more than one cycle of said oscillations.

6. A distance measurement system according to claim 1, wherein said amplitude envelope property is an amplitude rate of decay.

7. A distance measurement system according to claim 1, wherein said analyzer is operable to determine the distance between said resonant circuit and said magnetic element additionally from frequency properties of said oscillations.

8. A distance measurement system according to claim 1, comprising more than one resonant circuit, to thereby determine more than one distance between said resonant circuits and said at least one magnetic element.

9. A distance measurement system according to claim 8, operable to determine the distance between said resonant circuits and said at least one magnetic element in more than one dimension.

10. A distance measurement system according to claim 8, wherein said more than one resonant circuits are operable to resonate at different frequencies.

11. A distance measurement system according to claim 1, comprising more than one magnetic element, to thereby determine more than one distance between said at least one resonant circuit and said magnetic elements.

12. A distance measurement system according to claim 11, operable to determine the distance between said at least one resonant circuit and said magnetic elements in more than one dimension.

13. A distance measurement system according to claim 1, comprising more than one resonant circuit and more than one magnetic element, to thereby determine more than one distance between said resonant circuits and said magnetic elements.

14. A distance measurement system according to claim 13, operable to determine the distance between said resonant circuits and said at least one magnetic element in more than one dimension.

15. A distance measurement system according to claim 1, wherein said analyzer comprises a look-up table, comprising relationships between measured oscillations and distances.

16. A distance measurement system according to claim 15, wherein said relationships are per-system relationships.

17. A distance measurement system according to claim 15, wherein said relationships comprise in-situ calibrations.

18. A method for assembling a distance measurement system, comprising the steps of:
   placing a resonant circuit at a first location;
   placing a magnetic element with predetermined magnetic properties at a second location remote from said first location by a first distance;
   separately from said resonant circuit providing:
      a transmitter for transmitting an electromagnetic pulse to said resonant circuit;
      a detector for detecting oscillations emitted by said resonant circuit in response to said electromagnetic pulse; and,
      an analyzer for analyzing an amplitude envelope decay pattern, following said electromagnetic pulse, of said detected oscillations, therefrom to determine an eddy current factor effecting said decay pattern and therefrom to determine said first distance.

19. A method for assembling a distance measurement system according to claim 18, wherein said analyzer comprises a look-up table of relationships between measured oscillations and distances, and wherein said look-up table values are established for each one of a predetermined set of distances by performing for each predetermined distance the steps of:
   transmitting an electromagnetic pulse to said resonant circuit;
   detecting oscillations emitted by said resonant circuit in response to said electromagnetic pulse; and,
   measuring an amplitude envelope property of said detected oscillations, to thereby establish a look-up table value for said distance.

20. A method for measuring the distance between a first location comprising a resonant circuit and a second location comprising a magnetic element and having a first distance therebetween, comprising remotely from said first and said second locations carrying out the steps of:
   transmitting an electromagnetic pulse to said resonant circuit;
   detecting oscillations emitted by said resonant circuit in response to said electromagnetic pulse; and,
   analyzing an amplitude envelope decay pattern of said detected oscillations following said electromagnetic pulse, therefrom to determine an eddy current factor effecting said decay pattern and therefrom to determine said distance.

21. A method for measuring the distance between locations according to claim 20, wherein the step of analyzing an amplitude envelope property further comprises:
   comparing information detected from said emitted oscillations to information in a look-up table, of relationships between measured oscillations and distances.

22. A method for measuring the distance between locations according to claim 20, comprising obtaining said amplitude envelope property from an absolute value of amplitudes of said oscillations.

23. A method for measuring the distance between locations according to claim 20, comprising obtaining said amplitude envelope property from relative amplitude values of more than one cycle of said oscillations.

24. A method for measuring the distance between locations according to claim 20, comprising making use of an amplitude rate of decay as said amplitude envelope property.

25. A method for measuring the distance between locations according to claim 20, comprising additionally detecting the distance from frequency properties of said detected oscillations.

26. A distance measurement system utilizing eddy currents for energy dissipation, the system comprising:
   at least one resonant circuit;
   at least one magnetic element with predetermined magnetic properties located at a first distance from said resonant circuit;
   a transmitter operable to transmit an electromagnetic pulse; and
   a separate device, not connected to said resonant circuit, said separate device comprising:
      a receiver operable to detect oscillations emitted by said resonant circuit in response to said electromagnetic pulse; and,
      an analyzer operable to analyze an amplitude envelope decay pattern of said oscillations following said electromagnetic pulse as an indicator of eddy current induced energy dissipation, to thereby determine said first distance between said resonant circuit and said magnetic element.

* * * * *